(12) United States Patent
Bakar et al.

(10) Patent No.: US 9,751,929 B2
(45) Date of Patent: Sep. 5, 2017

(54) METHOD OF USING PAPAIN TO EXTRACT COLLAGEN FROM AQUATIC ANIMALS

(71) Applicant: Universiti Putra Malaysia Serdang, Selangor Darul Ehsan (MY)

(72) Inventors: Jamilah Bakar, Selangor Darul Ehsan (MY); Umi H. Razali, Selangor Darul Ehsan (MY); Dzulkifly M. Hashim, Selangor Darul Ehsan (MY); Awis Q. Sazili, Selangor Darul Ehsan (MY); Kaur Harvinder, Selangor Darul Ehsan (MY)

(73) Assignee: Universiti Putra Malaysia Serdang, Selangor Darul Ehsan (MY)

( * ) Notice: Subject to any disclaimer, the term of this patent is extended or adjusted under 35 U.S.C. 154(b) by 553 days.

(21) Appl. No.: 14/170,396

(22) Filed: Jan. 31, 2014

(65) Prior Publication Data

US 2014/0147400 A1 May 29, 2014

Related U.S. Application Data (63) Continuation of application No. 13/158,954, filed on Jun. 13, 2011, now abandoned.

(51) Int. Cl.
*C07K 14/78* (2006.01)
*C07K 14/46* (2006.01)
*G01N 33/68* (2006.01)

(52) U.S. Cl.
CPC ............ *C07K 14/78* (2013.01); *C07K 14/461* (2013.01); *G01N 33/6887* (2013.01)

(58) Field of Classification Search
None
See application file for complete search history.

(56) References Cited

U.S. PATENT DOCUMENTS

| 5,093,474 A | 3/1992 | Grossman et al. |
| 6,548,077 B1 | 4/2003 | Gunasekaran |

OTHER PUBLICATIONS

Skierka et al., The influence of different acids and pepsin on the extractability of collagen from the skin of Baltic cod (*Gadus morhua*), Food Chemistry, 2007, vol. 105, pp. 1302-1306.
Kaur, H., Extraction and Characterisation of Collagen and Gelatin From Red Tilapia (*Oreochromis nilotica*) Skin, Master of Science Thesis at the Universiti Putra Malaysia, 2006, pp. ii-3.
Jamilah et al., Properties of gelatins from skins of fish-black tilapia (*Oreochromis mossambicus*) and red tilapia (*Oreochromis nilotica*), Food Chemistry, 2002, vol. 77, pp. 81-84.
Friedman M., Nature Letters, Jul. 10, 2008, vol. 454, pp. 209-212.

*Primary Examiner* — Ralph Gitomer
(74) *Attorney, Agent, or Firm* — Locke Lord LLP; Ralph A. Loren; Nicholas J. DiCeglie, Jr.

(57) ABSTRACT

Disclosed is a method of using papain to extract collagen from the skin of aquatic animals. The method comprising using papain to obtain collagen by introducing the collagen fibers into a sodium chloride solution; collecting the collagen fibers and centrifuging the collagen fibers for at least 20 minutes; and obtaining a collagen yield of between 14 and 40% by weight.

2 Claims, 4 Drawing Sheets

Figure1: SDS-PAGE Patterns of Collagen from Skins of Red Tilapia

M: molecular weight marker; T: trypsin digested collagen;
Pa: Papain-digested collagen; P: pepsin-digested collagen.
Tp = gel top and F = buffer front Figure 2: SDS-PAGE Patterns of Collagen from Skins of Red Tilapia as Affected by Different Enzyme Extraction and Storage Study M: molecular weight marker; T: trypsin digested collagen; Pa: Papain-digested collagen; P0: pepsin 0-week storage; P4: pepsin 4-weeks storage; P6: pepsin 6-weeks storage; P8: pepsin 8-weeks storage. Tp = gel top and F = buffer front.

Figure 3 represents an electrophoretic pattern of collagen samples from barramundi skin with comparison to type 1 collagen from calf skin Figure 4: Energy Dispersive X-ray (EDX) Chromatogram of Collagen Sample from Red Tilapia Skins

METHOD OF USING PAPAIN TO EXTRACT COLLAGEN FROM AQUATIC ANIMALS

RELATED APPLICATIONS

This application is a continuation of U.S. patent application Ser. No. 13/158,954, filed Jun. 13, 2011, now abandoned which is a continuation of PCT application No. PCT/MY2009/000122, filed on Aug. 19, 2009, which claims priority to Malaysian Patent Application No. PI 20085247, filed on Dec. 23, 2008, the entirety of which is incorporated herein by reference.

FIELD OF INVENTION

The present invention relates to a collagen obtained from fishes and a method of producing such fish collagen. In particular, the present invention is directed to a collagen obtainable from the skin of fishes and a method of extracting and producing the same.

BACKGROUND OF INVENTION

A great amount of waste portions of fish, which are generally considered useless or untapped, had been discarded. This has been one of the major problems that we should address in the modern society to find various ways to use that seemingly unserviceable portion of fishes in many applicable fields. In view of collagen being obtained from mammals and widely available as an edible material, researches are now being made about fish collagen and in particular about salmon and trout skins, in which a collagen is a main ingredient of the tissues. Recent years, thus, have seen some methods proposed to extract and produce a collagen from fish skins, including the skins of salmon and trout in question. The fish skin collagen, however, differs in characteristics from mammalian collagen and requires relatively less harse treatment due to the more delicate matrix of the skin. Collagen products have a number of applications in various industries. In one such application, collagen powders are used in clarification or precipitation processes, for example for clarifying potable liquors such as beer and wine. During the fermentation of liquors various particulate materials such as yeasts and proteins become suspended in the liquor and need to be removed. Collagen findings are added to the liquor to clarify it by aiding the precipitation of the suspended materials. Collagen and gelatin can also be used in juice clarification processes.

Collagen is generally prepared from fish isinglass, which constitutes a very pure source of collagen prepared from the dried swim bladders of fish. Many investigations have been made into the extraction of collagen from animal and fish skins including cold water fish skins (U.S. Pat. Nos. 4,295,894, 5,698,228, 5,162,506, 5,420,248, JP 4037679, JP 9278639, JP 2-291814, PL 312122, RU 2139937). The collagen extraction processes known involve a wide range of chemical and mechanical extractions, or combinations thereof. The properties of the collagen products obtained by these processes vary widely. Many of the extraction processes applied to fish skins are adaptations and modifications of mammalian collagen extraction techniques. The applicants have identified that many of the processing steps applied to mammalian collagen extraction are not directly applicable for fish skin collagen extraction since the treatment may be quite harsh or too strong for the fish skin matrix. Such steps include chemical washes and extractions with strong acids or alkali, excessive filtering and decantation steps amongst others. A simplified extraction process which eliminates many of these steps would be desirable to increase yield and to reduce denaturation of the extracted collagen.

Collagen is recognized as a difficult and expensive protein to quantify because of the insoluble nature of most collagens. Yet, solubility is a key functional property important in a variety of applications such as healthcare products. The applicants have also determined that the conformation of the native collagen molecule determines molecular functionality, with transition to the random coiled confirmation of gelatin upon denaturing resulting in a significant loss in fining ability. Collagen has also been reported to be extracted from several fish species such as hake (*Merluccius merluccius* L.), yellow sea-bream (*Dentex tumiforms*), tiger puffer (*Takifugu rubripes*), carp (*Cyprimus carpio*); squids (*Illex argentinus*) (Ilona Kolodziejska, 1999); and also jellyfish (*Rhopilema asamushi*) (Takeshi Nagai et. al, 2000). All procedures reported were very similar where non-enzymatic extractions were employed and, if enzymatic reactions were used, then pepsin was the most common enzyme.

The use of by-products from fish processing for collagen and gelatine production, as an alternative introduces some questions, the diversity of aquatic species and also the higher susceptibility of this collagen to deterioration when compared to those from mammals, which is more stable and facilitates its preservation (Fernandez-Diaz et al., 2003). Moreover, after degutting and filleting of fish, skins are kept with the rest of the discard and they are subjected to rapid enzymatic and microbial damage, which are natural and this may lead to quality variation of the extracted collagen and the gelatins. Enzymatic activities in aquatic animals are known to be higher than land animals.

Collagen exists in several polymorphic forms, the common ones are Type I, III and V; type II and IV which are uncommon and can only be found in certain collagens, which have also been reported (Foegeding et al., 2001). Collagens and their denatured forms, gelatines, are composed of long chains of amino acids, connected by peptide bonds (Ockerman and Hansen, 1988; Ward and Courts, 1977). The number and type of chemical covalent bonds between the chains are altered as the animal ages, fewer numbers in younger animals. This influences the molecular properties of the resultant gelatine and glue (Ockerman and Hansen, 1988). Fish collagens, in general, have lower amino acids contents than mammalian collagens and this may be the reason for the lower denaturation temperature (Grossman and Bergman, 1992, Jamilah and Harvinder, 2002). This in turn appears to be related to the body temperature of the species (Johns, 1977). There are many properties of collagen that make it an attractive substance for various medical applications, such as for implants, transplants, organ replacement, tissue equivalents, vitreous replacements, plastic and cosmetic surgery, surgical suture, surgical dressings for wounds, burns, etc. (See e.g., U.S. Pat. Nos. 5,106,949, 5,104,660, 5,081,106, 5,383,930, 4,485,095, 4,485,097, 4,539,716, 4,546,500, 4,409,332, 4,604,346, 4,835,102, 4,837,379, 3,800,792, 3,491,760, 3,113,568, 3,471,598, 2,202,566, and 3,157,524, all of which are incorporated herein by reference; Prudden, Arch. Surg. 89:1046-1059 [1964]; and Peacock et al. Ann. Surg., 161:238-247 [1965]). For example, by itself, collagen is a relatively weak immunogen, at least partially due to the masking of potential antigenic determinants within the collagen structure. Also, it is resistant to proteolysis due to its helical structure. In addition, it is a natural substance for cell adhesion and the major tensile load-bearing component of the musculoskeletal system. Thus, extensive efforts have been devoted to the production of collagen fibers and membranes suitable for use in medical, as well as veterinary applications. Collagens have been actively incorporated in beverage formulations (both instant and traditional), of late.

SUMMARY OF INVENTION

The present invention relates to a process of extracting collagen (type 1 collagen), the collagen is obtained from skins of aquatic animals (preferably Lates calcarifer and Oreochromis nilotica). The collagen is extracted from fish skin using an enzyme, whereby the enzyme is papain. Furthermore, the process comprises a starting material consisting essentially of fish skin, extracting collagen from said the fish skin, and recovering the collagen. The skin is obtained by removing the skin from fresh or frozen fish. Moreover, the process further includes: extracting collagen from skins of Lates calcarifer (barramundi) which includes mixing the skin with alkaline solution (such as sodium) for at least 6 hours; washing the skin with water to eliminate residual of alkaline; soaking the skin with an alcohol (such as butyl alcohol) solution for at least 18 hours; washing the skin with a neutral solution; treating the skin with an acidic solution; hydrolyzing the skin with papain; obtaining a mixture and stirring the mixture at a working temperature of 4° C. for at least 24 hours; centrifuging the mixture at 4° C.; precipitation of collagen by introducing the collagen into a sodium chloride solution to precipitate collagen fibers; collecting the collagen fibers and centrifuging the collagen for at least 60 minutes thus obtaining collagen pellet; dissolving the collagen pellet into acetic acid solution and/or freeze-drying the dialysed suspension.

In addition, the process of extracting collagen from skins of Oreochromis nilotica (red tilapia) further includes; homogenizing the fish skin with alkaline solution such as sodium; obtaining a suspension and stirring the suspension for at least 24 hours; centrifuging the suspension for at least 20 minutes; obtaining a precipitate; homogenizing the precipitate with alkaline solution; stirring the precipitate for at least 24 hours and for at least 3 repeats; washing the precipitate with water and acetic acid solution; stirring the precipitate with papain at a working temperature of 4-5° C. for at least 24 hours; obtaining a mixture; centrifuging the mixture for at least 20 minutes; obtaining collagen fibers; introducing the collagen into a sodium chloride solution; collecting the collagen fibers and centrifuging the collagen for at least 20 minutes; as a result collagen pellet is obtained; and freeze-drying the dialysed suspension. The collagen obtained from the skin/s of Lates calcarifer and Oreochromis nilotica having a percentage of working yield between 14 and 40% by wet weight. The characterization of the properties of the extracted collagen) analysis of the followings: amino acid analysis, peptide in the collagen and type of collagen. The amino acid which was obtained includes glycine, proline, alanine and arginine. The peptide obtained had an apparent molecular weight distribution of 37 and 205 kilodalton (kDa).

In addition, the present invention also relates to the use of the collagen for the manufacture of a pharmaceutical composition cosmetic or topical preparation or food product/s. The cosmetic includes cream, eye cream, lotion, ointment or gel, sun-screen, oral administration, face mask cream, anti-inflammatory medicine, and/or anti-irritant medicine. The food product/s include(s) beverages, dairy products, confectionaries, chocolates, and any application in food formulation/s as an ingredient or for any functional properties.

DETAILED DESCRIPTION OF THE INVENTION

The present invention relates to methods for preparing collagen from aquatic animals. In particular, the present invention provides methods for the preparation of collagen suitable as the raw material for biomedical, and pharmaceutical applications; and for food application.

Definitions

Creams, as is a well-known arts of pharmaceutical and cosmeceutical composition, are viscous liquids and semi-solids emulsions, either oil-in-water or water-in-oil. Cream bases are water-washable, and contain an oil phase, and emulsifier, and an aqueous phase. The aqueous phase usually exceeds the oil phase in volume, and generally contains substance. The emulsifier is a cream composition generally nonionic, anionic, cationic or amphoteric surfactant.

The creams, lotions, gels, emulsions and paste or the like may be spread on the affected surface and gently rubbed in. A solution may be applied with a measuring device, swab, or the like, and carefully applied to the affected areas.

Unless stated otherwise, the amounts are given in % by weight, based on the total weight of the respective preparations.

The present invention relates to the use of fish skin as novel industrial source of collagen. Advantageously, said skin is obtained after the filleting or cutting of the fresh fish and frozen immediately after filleting/cutting, thus guaranteeing a very good quality of the base material, both from the standpoint of bacteriological and the native properties of the protein.

EXAMPLES

Materials

Red tilapia (Oreochromis nilotica) is a cultured freshwater fish obtained from a local fish farm in Ulu Langat, Selangor. The red tilapia weighed between 500 g to 600 g. Upon arrival at the laboratory, the fish were killed, filleted and the skin was manually removed. The skins were stored at −20° C. until to be used.

Chemicals

Pepsin (crystallized and lyophilized, EC 3.4.23.1, from porcine stomach mucosa) with a declared activity of 3460 units/mg protein was obtained from Sigma Chemical. Trypsin (crystallized and lyophilized, EC 3.4.21.4 from porcine pancreas) with a declared activity of 40 U/mg protein and Papain (dry powder, EC 3.4.22.2, from Carica papaya) with a declared activity of 30000 USP-U/mg were obtained from Merck (USA). All other chemicals used were of analytical grade.

BEST MODE TO CARRY OUT THE INVENTION

Extraction

Storage study of the red tilapia skins was also carried out to determine the effects of frozen storage on collagen characteristics Skins were stored frozen up to 8 weeks and subjected to treatments at 2 weeks interval. The fish skins were cut into small pieces with scissors and thoroughly rinsed in excess water to remove superfluous material. They were then homogenized with 10 volumes of 0.1 M NaOH to remove non-collagenous proteins and to prevent the effect of endogenous proteases on collagen (Sato and others, 1987). The suspension was stirred overnight and centrifuged at 10000×g for 20 min. The resultant precipitate was rehomogenized with 20 volumes of 0.1 M NaOH and stirred slowly overnight. This procedure was repeated 3 or 4 times. The residue after alkali extraction was carefully and gently washed with distilled water and then suspended in 0.5 M acetic acid.

The suspension was then stirred with enzyme at an enzyme/substrate ratio of 1/1000 (w/w) for 24 h at 5° C. Enzymes used were pepsin, trypsin and papain. The suspension was then centrifuged at 10000×g for 20 min. The collagen in the resultant supernatant after centrifugation was salted out by adding NaCl to give a final concentration of 2.0 M. After centrifugation at 10000×g for 20 min, the resultant precipitate was freeze-dried.

Analyses

Yield of collagen (% w/w)

Yield is determined by weight of collagen extracted as to weight of wet skins used. Yield is calculated as follows.

$$\text{Yield (\% w/w)} = \frac{\text{collagen (dry weight)}}{\text{Fish skins(Wet weight)}} \times 100\%$$

Visual Observations and Instrumental Colour

Visual observations for colour and texture were also noted. Colour measurements were made using Hunterlab Ultrascan Sphere Spectrocolorimeter (model Minolta Cr-300 Series). The samples were filled in a clear plastic and readings were then taken. Readings were carried out in triplicates.

Yields of dried collagens obtained from red tilapia skins (Oreochromis nilotica) are shown in Table 1. Yield is calculated based on the dry weight of collagen over the wet weight skins. These yields are in the range as those reported by Takeshi and Nobutaka (2000) for Japanese-sea-bass (55.4%), chub mackerel (49.8%) and bullhead shark (50.1%). Nagai et al., (2000) recorded a yield of 35.2% on a dry weight basis of collagen extracted from rhizostomous jellyfish. Pepsin-digested extraction 0-week storage collagen recorded the highest yield of 74.77±11.36% followed by pepsin-digested extraction 4-week storage of 63.62±6.05% and pepsin-digested extraction 8-week storage of 62.98±2.37%. The lowest yield was recorded by trypsin-digested extraction 0-week storage i.e. 31.59±5.95%.

In the storage study, 0-week storage gave the highest yield of 74.77% followed by 4-weeks storage (63.62%) and 8-weeks storage 62.98%. Lowest yield is recorded by 2-weeks storage (37.66%). This lower yield could be due to the loss of extracted collagen through leaching during the series of washings steps. Thus, lower concentrations of collagen were extracted. Another possible reason for the lower yield could be due to the incomplete hydrolysis of the collagen. The extraction time and temperature combination may not be sufficient enough to allow complete hydrolysis of the collagen. Protein composition of the tilapia skins may also influence the yield of collagen obtained.

TABLE 1

Yield (%) and Protein Content (%) of Collagen Samples from Red Tilapia Skins

| Collagen Sample | Yield And Protein Content of Collagen Samples | |
|---|---|---|
| | Yield (%) | Protein Content (%) |
| Papain-digested | 40.15 ± 4.55$^{CD}$ | 25.83 ± 1.01$^{B}$ |
| Trypsin-digested | 31.59 ± 8.41$^{D}$ | 30.15 ± 0.83$^{A}$ |
| Pepsin-0-week | 74.77 ± 16.07$^{A}$ | 14.24 ± 1.26$^{E}$ |
| Pepsin-2-week | 37.66 ± 7.58$^{CD}$ | 26.29 ± 0.40$^{B}$ |
| Pepsin-4-week | 63.62 ± 6.05$^{AB}$ | 15.65 ± 2.96$^{E}$ |
| Pepsin-6-week | 51.51 ± 7.81$^{BcD}$ | 20.09 ± 0.59$^{D}$ |
| Pepsin-8-week | 62.98 ± 2.37$^{AB}$ | 24.68 ± 0.40$^{B}$ |

Values are the means ± standard deviations of 3 replicates.
Means with the same superscripts within each column are not significantly different ($p < 0.05$).

Protein Content

Protein content was determined by the micro-Kjedhal method (AOAC, 1995) and a nitrogen conversion factor of 5.3 was used. Protein digestion was done with concentrated sulfuric acid to ensure complete hydrolysis of collagen. Analyses were carried out in triplicates. Protein content of trypsin-digested collagen was twice the protein content of pepsin-digested collagen; 30.15% and 14.24% respectively. Papain-digested collagen has a protein content of 25.83% which is lower than trypsin-digested collagen. In the storage study, 0-week storage and 4-weeks storage have the lowest protein content (<15%) whereas 2-weeks storage had the highest protein content of 26.29%.

Visual Observation and Instrumental Color

The visual observation is as shown in Table 2. All samples except papain digested collagen were of snowy white and light-textured. Papain digested collagen however, has light yellow and was light-textured in appearance. Plate 1 and 2 shows the collagen samples extracted by different enzymes and storage study respectively.

TABLE 2

Visual Observation of Red Tilapia Skin Collagen as Extracted By Different Enzymes and Storage Study.

| Collagen Samples | Appearance |
|---|---|
| Trypsin digested | Snowy white and light-textured |
| Papain digested | Light yellow and light-textured |
| Pepsin 0-week | Snowy white and light-textured |
| Pepsin 2-week | Snowy white and light-textured |
| Pepsin 4-week | Snowy white and light-textured |
| Pepsin 6-week | Snowy white and light-textured |
| Pepsin 8-week | Snowy white and light-textured |

Table 3 shows the Hunter values of collagen extracted by different enzymes and storage study. The L*, a* and b* values were quite similar for all collagen samples. L* value which indicates the lightness value was >93 for all samples. This shows that all samples extracted by different enzymes and subjected to storage study were white in colour and this corresponds with the visual observation made. The negative a* values (−a) also shows a slight red hue in all samples whereas the higher b* value indicates more yellowish hue.

However, papain digested collagen sample has the highest b* value, thus more yellowish in appearance. Furthermore, Table 3 illustrates all samples L* value of >95 indicating whiter samples. However, the b* value of pepsin 6-week collagen sample was the lowest compared to other samples. Nevertheless, the L*, a* and b* values for all samples in the storage study were almost similar and not much difference were observed which corresponds with the visual appearance of the thus samples. The colour of the collagen depends on the raw material. However, it does not influence other functional properties (Ockerman and Hansen, 1988).

TABLE 3

Instrumental Color of Collagen Samples As Affected by Different Enzyme Extractions and Storage Period

| Sample | Instrumental Colour | | |
|---|---|---|---|
| | L | a | b |
| Trypsin digested | $95.62 \pm 0.07^{Bc}$ | $-1.10 \pm 0.04^{EF}$ | $6.38 \pm 0.49^{Bc}$ |
| Papain digested | $94.63 \pm 0.30^{D}$ | $-0.65 \pm 0.04^{B}$ | $7.24 \pm 0.37^{A}$ |
| Pepsin 0-week | $95.70 \pm 0.67^{Bc}$ | $-0.49 \pm 0.09^{A}$ | $6.77 \pm 0.82^{AB}$ |
| Pepsin 2-week | $95.85 \pm 0.10^{Bc}$ | $-1.01 \pm 0.02^{E}$ | $5.06 \pm 0.25^{DE}$ |
| Pepsin 4-week | $97.23 \pm 0.10^{A}$ | $-0.80 \pm 0.04^{c}$ | $5.15 \pm 0.15^{DE}$ |
| Pepsin 6-week | $96.89 \pm 0.16^{A}$ | $-0.62 \pm 0.06^{B}$ | $4.47 \pm 0.08^{E}$ |
| Pepsin 8-week | $95.94 \pm 0.27^{B}$ | $-0.90 \pm 0.07^{D}$ | $5.73 \pm 0.40^{cD}$ |

Values are the means ± standard deviations of 3 replicates.
Means with the same superscripts within each row are not significantly different ($p < 0.05$)

TABLE 4 represents physic-chemical properties of collagen from Barramundi skins.

| Properties | Control | Pepsin-extracted | Papain-extracted |
|---|---|---|---|
| Yield (%) | 2.8 | 14.0 | 14.1 |
| Protein content (%) | $68.72 \pm 0.95$ | $92.82 \pm 2.68$ | $111.16 \pm 1.05$ |
| Moisture content (%) | $18.46 \pm 1.23$ | $18.55 \pm 0.67$ | $16.05 \pm 0.31$ |
| Hunter color values | | | |
| 'L' | $65.41 \pm 0.08$ | $61.33 \pm 0.04$ | $44.76 \pm 0.02$ |
| 'a' | $0.14 \pm 0.01$ | $2.59 \pm 0.02$ | $0.74 \pm 0.02$ |
| 'b' | $3.16 \pm 0.03$ | $5.35 \pm 0.04$ | $2.14 \pm 0.04$ |

Amino Acids Composition

The amino acids composition in collagen was determined using Waters-Pico Tag Amino Acid Analyzer High Performance Liquid Chromatography, Model: Waters 501 Millipore Corporation, USA with column size 3.9×150 mm. Each sample was hydrolyzed with 6 N HCl at 110° C. for 24 hrs. The hydrolysis was analyzed for their free amino acid content on a Waters auto analyzer, as recommended in the Waters-501 Instruments Manual (1991). Table 5 shows the amino acid composition of the collagen from red tilapia skins due to different enzyme extractions and storage periods. The amino acid profile obtained was from an acid hydrolysate. The amino acid content of trypsin and papain-digested collagen are higher than that of pepsin-digested collagen. The amino acid profile of papain and trypsin-digested collagen are not significantly different (p<0.05).

TABLE 5

Amino Acids Composition in Various Species of Fish Collagen

| Amino Acids | Amino Acid Content (mg/g sample) | | | |
|---|---|---|---|---|
| | Red Tilapia[a] | C H Mackerel[b] | Y S Bream[b] | Tiger Puffer[b] |
| Asp | $4.5 \pm 0.2$ | $42.9 \pm 1.4$ | $40.7 \pm 0.9$ | $44.6 \pm 0.4$ |
| Glu | $11.0 \pm 0.1$ | $72.5 \pm 0.6$ | $72.6 \pm 1.2$ | $68.0 \pm 0.3$ |
| Ser | $11.9 \pm 0.4$ | $35.8 \pm 0.2$ | $41.2 \pm 0.6$ | $42.9 \pm 0.4$ |
| Gly | $71.9 \pm 0.3$ | $361.5 \pm 0.3$ | $351.3 \pm 2.0$ | $349.9 \pm 2.1$ |
| His | ND | $4.4 \pm 0.0$ | $3.8 \pm 0.2$ | $3.6 \pm 0.1$ |
| Arg | $35.6 \pm 0.8$ | $53.0 \pm 0.4$ | $52.0 \pm 1.3$ | $52.7 \pm 0.1$ |
| Thr | $10.8 \pm 0.1$ | $30.1 \pm 0.4$ | $29.8 \pm 0.5$ | $29.1 \pm 0.5$ |
| Ala | $37.3 \pm 0.4$ | $120.6 \pm 0.7$ | $124.7 \pm 1.2$ | $117.5 \pm 1.6$ |
| Pro | $55.8 \pm 0.9$ | $115.2 \pm 2.2$ | $110.7 \pm 0.4$ | $112.5 \pm 0.3$ |
| Tyr | $3.2 \pm 0.4$ | $1.5 \pm 0.1$ | $2.0 \pm 0.0$ | $1.6 \pm 0.1$ |
| Val | $8.0 \pm 0.0$ | $16.1 \pm 0.4$ | $16.3 \pm 0.3$ | $21.7 \pm 0.0$ |
| Met | $6.0 \pm 1.1$ | $10.1 \pm 0.9$ | $11.4 \pm 2.0$ | $14.0 \pm 0.2$ |
| Cys | ND | ND | ND | ND |
| Ile | $5.1 \pm 0.1$ | $8.2 \pm 0.2$ | $6.9 \pm 0.1$ | $7.4 \pm 0.0$ |
| Leu | $11.4 \pm 0.2$ | $18.7 \pm 0.1$ | $17.0 \pm 0.7$ | $15.4 \pm 0.2$ |
| Phe | $6.5 \pm 4.9$ | $11.2 \pm 0.0$ | $12.2 \pm 0.5$ | $12.3 \pm 0.1$ |
| Lys | $10.9 \pm 0.7$ | $23.7 \pm 0.9$ | $25.6 \pm 1.3$ | $29.0 \pm 1.8$ |
| Total | 289.9 | 925.5 | 918.2 | 922.2 |

ND—Not Detected
[a]Trypsin digested collagen results
[b]Sourced from Yata et al. (2001)

The total amino acids content increases gradually from 4th to 8th week storage. Glycine and proline are the major amino acids, constituting a quarter and a fifth of total amino acid content of the collagen samples respectively. This characteristic distinguishes collagen from other proteins. Proline content in both trypsin (55.81) and papain-digested (51.54) collagens are double than in pepsin-digested 0-week storage (25.95). However, in this present invention, hydroxyproline content could not be determined. These compositions are different from which was reported from horse mackerel, yellow seabream and tiger puffer.

TABLE 6 represents Amino acids composition of collagen from Barramundi skins

| Amino acid (g/100 g) | Control | Pepsin-extracted | Papain-extracted |
|---|---|---|---|
| Aspartic acid | $3.797 \pm 0.14$ | $4.075 \pm 0.19$ | $4.038 \pm 0.05$ |
| Serine | $1.927 \pm 0.07$ | $1.989 \pm 0.09$ | $2.30 \pm 0.03$ |
| Glutamic acid | $6.847 \pm 0.25$ | $7.061 \pm 0.35$ | $7.256 \pm 0.10$ |
| Glycine | $14.992 \pm 0.56$ | $15.539 \pm 0.76$ | $19.208 \pm 0.31$ |
| Histidine | $1.449 \pm 0.04$ | $1.298 \pm 0.02$ | Not detected |
| Arginine | $5.943 \pm 0.07$ | $6.38 \pm 0.06$ | $8.316 \pm 0.08$ |
| Threonine | $2.066 \pm 0.05$ | $2.171 \pm 0.02$ | $2.485 \pm 0.02$ |
| Alanine | $6.996 \pm 0.27$ | $6.865 \pm 0.20$ | $8.890 \pm 0.12$ |
| Proline | $7.887 \pm 0.21$ | $7.543 \pm 0.18$ | $12.772 \pm 0.07$ |
| Cysteine | Not detected | Not detected | Not detected |
| Tyrosine | $0.258 \pm 0.01$ | $0.4925 \pm 0.03$ | $0.298 \pm 0.01$ |
| Valine | $1.739 \pm 0.07$ | $1.8715 \pm 0.09$ | $2.080 \pm 0.03$ |
| Methionine | $1.299 \pm 0.06$ | $1.345 \pm 0.16$ | $1.676 \pm 0.48$ |
| Lysine | $2.561 \pm 0.09$ | $2.872 \pm 0.14$ | $2.338 \pm 0.01$ |
| Isoleucine | $0.903 \pm 0.04$ | $1.063 \pm 0.05$ | $1.135 \pm 0.02$ |
| Leucine | $1.664 \pm 0.07$ | $1.931 \pm 0.09$ | $2.229 \pm 0.03$ |
| Phenylalanine | $1.436 \pm 0.09$ | $1.369 \pm 0.15$ | $1.898 \pm 0.02$ |
| Total | 61.40 | 63.862 | 76.919 |

Molecular Weight Determination

Figure 1:
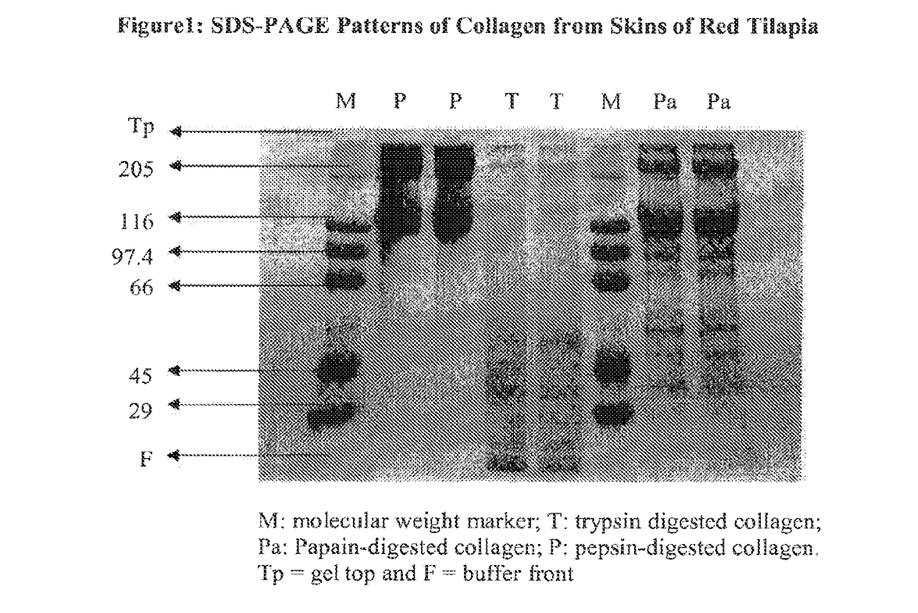
FIG. 1 shows SDS-PAGE Patterns of Collagen from Skins of Red Tilapia.
Figure 2:
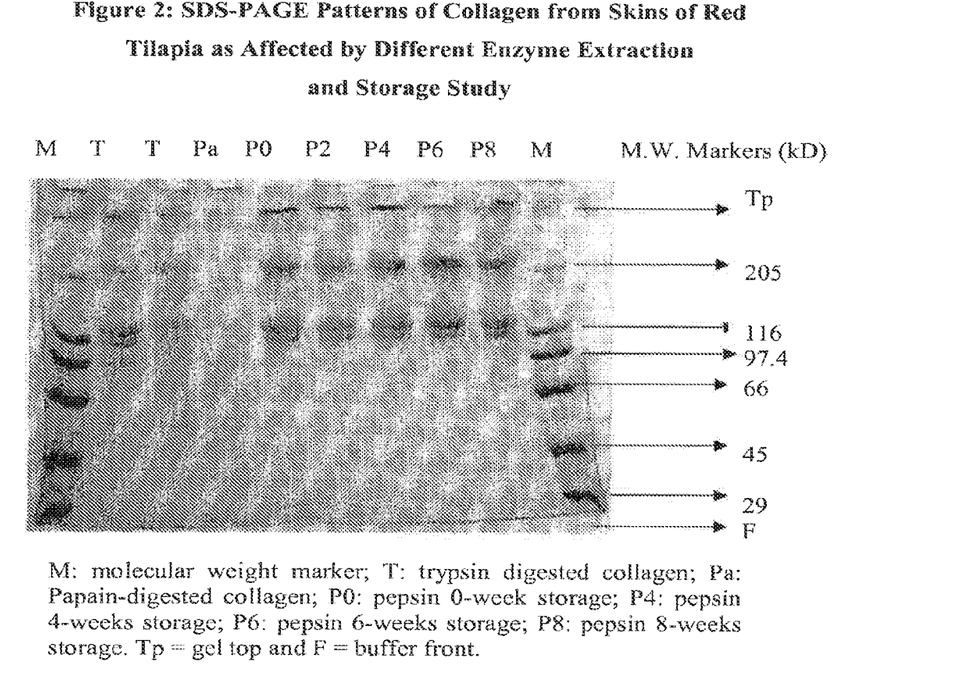
FIG. 2 shows SDS-PAGE Patterns of Collagen from Skins of Red Tilapia as Affected by Different Enzyme Extraction and Storage Study.

Molecular weight was determined by SDS-PAGE (Laemmli, 1970) and the run was made in a 5% T gel containing 0.1% SDS. Molecular weight marker SDS-6H (Sigma) was used as the standard. Samples (4-50 µg/well) were applied to the gel and the gel was stained for protein with Coomassie Brilliant Blue R-250. FIGS. 1 and 2 shows the SDS-PAGE patterns of collagen from skins of red tilapia extracted with different enzymes and storage period respectively. Visually 16, 15 and 7 bands were observed for trypsin, papain and pepsin-digested extraction respectively. Apparent molecular weights of peptide detected were in the range of 20,300 Da to 221,900 Da for papain-digested extraction whereas 31,500 Da to 200,000 Da for trypsin-digested extraction. In pepsin-digested extractions (storage study), no peptide bands above 144,200 Da were observed. The molecular weight patterns for the storage study samples are also almost similar. Identification of the molecular bands associated with the types of collagens is the common results report for the SDS-PAGE electrophoresis.

Figure 3:
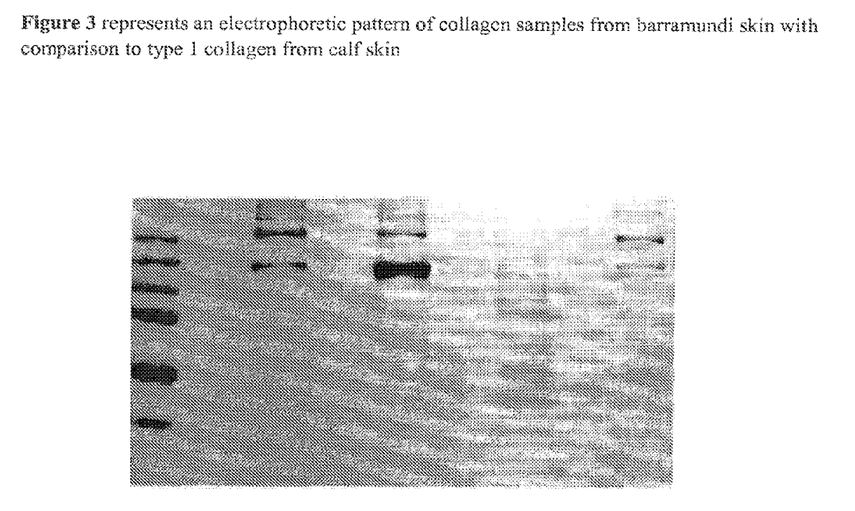
FIG. 3 shows an electrophoretic pattern of collagen samples from barramundi skin with comparison to type 1 collagen from calf skin.

FIG. 3 represents an electrophoretic pattern of collagen samples from barramundi skin with comparison to type 1 collagen from calf skin. Apparent molecular weights of peptide detected were in the range of ~30,000 to 250,000 kDa. Collagen from barramundi skin contained two different α chain ($α_1$ and $α_2$) and β-component. These electrophoretic patterns were similar to calf skin collagen and the kind of dimmer was also observed in collagen samples from other aquatic sources. The acid-soluble collagen and pepsin-soluble collagen had similar electrophoretic pattern with type 1 collagen from calf skin. However, papain-extracted collagen shows slightly different pattern, the β dimmer was not observed. Collagen with papain treatment also contained products of enzymatic hydrolysis below 100 kDa. This result suggested that different type of proteases have different cleavage properties of the collagen samples, as shown in the SDS-PAGE chromatogram.

Mineral Content

Figure 4:
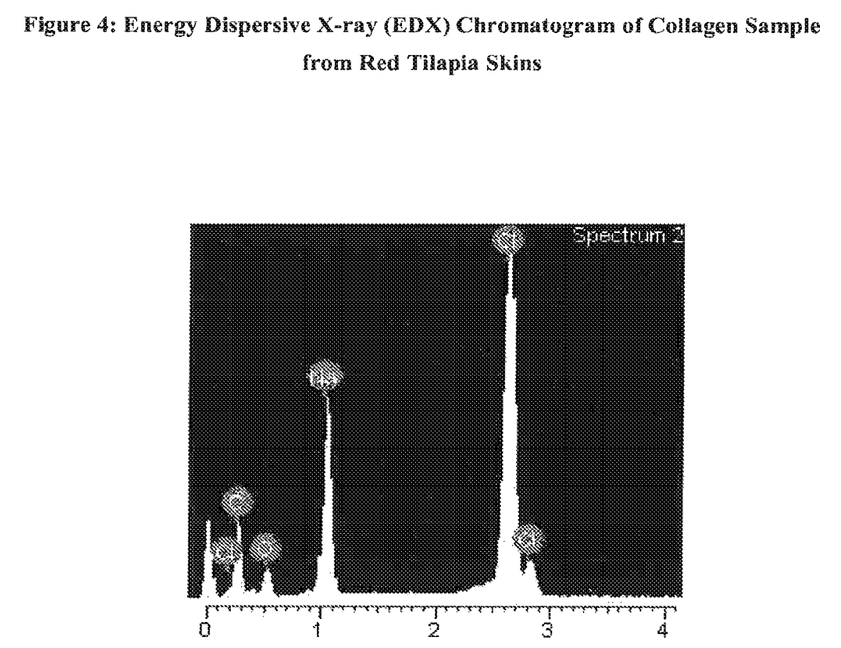
FIG. 4 shows Energy Dispersive X-ray (EDX) Chromatogram of Collagen Sample from Red Tilapia Skins.

Mineral analysis was determined using Energy Dispersive X-ray (EDX). The collagen sample was mounted onto the stub and viewed by EDX, using QBSD signal. Table 7 shows the mineral analysis of collagen from tilapia skins by different enzyme extractions and different storage period. Mineral analysis by EDX was carried out to determine the mineral elements of collagen obtained. Four elements were detected in all samples, namely carbon, oxygen, sodium and chlorine as shown by the EDX chromatogram (FIG. 4). Collagen is not a metalloprotein, therefore the absence of heavy metals indicates that these collagens are safe (GRAS). The presence of sodium and chlorine in all collagens are probably due to the effect of salting process (NaCl) to precipitate out collagen after extraction step. Trypsin-digested extraction showed the highest carbon and oxygen content of 48.64% and 7.69% respectively. Chlorine is the major element in all samples except for trypsin-digested extraction (33.61%). Oxygen is the minor element detected in all samples ranging from 1-7%. The carbon content indicates that the collagens are of organic matter.

To this date, there are no reported findings of mineral analysis of collagens.

TABLE 7

Mineral Analysis (in Weight %) of Collagen from Red Tilapia Skins by Different Enzyme Extraction and Storage Period

| Sample | Carbon | Oxygen | Sodium | Chlorine |
| --- | --- | --- | --- | --- |
| Trypsin 0-wk | 48.64 ± 4.03 | 7.69 ± 0.41 | 10.05 ± 1.11 | 33.61 ± 3.15 |
| Papain 0-wk | 21.54 ± 12.15 | 2.03 ± 1.49 | 18.72 ± 2.65 | 57.79 ± 11.15 |
| Pepsin 0-wk | 13.56 ± 2.89 | 1.02 ± 0.36 | 22.47 ± 0.36 | 65.95 ± 2.58 |
| Pepsin 2-wk | 30.04 ± 3.48 | 4.00 ± 0.99 | 11.45 ± 4.12 | 54.50 ± 7.56 |
| Pepsin 4-wk | 33.30 ± 0.94 | 4.32 ± 0.15 | 15.45 ± 0.40 | 46.92 ± 0.78 |
| Pepsin 6-wk | 12.07 ± 1.81 | 1.56 ± 0.35 | 20.49 ± 2.10 | 65.88 ± 3.73 |
| Pepsin 8-wk | 23.25 ± 3.15 | 2.33 ± 0.47 | 16.33 ± 1.68 | 58.09 ± 4.41 |

Values are the means ± standard deviations of 3 replicates.
Means with the same superscripts within each row are not significantly different ($p < 0.05$)

Storage Study

Skins were stored frozen (−20° C.) for up to 2 months. Every week, the skins were thawed and subjected to treatment to extract collagen. The collagen obtained was then analyzed as before to determine the effects of frozen storage of skins on the collagen characteristics.

Statistical Analysis

All data collected were analysed using the analysis of variance (ANOVA) and Duncan's Multiple Range Test to determine the significant differences between means (SAS, 1987). Extraction processes of collagen and the following treatments reflect the different quality of gelatine obtained. Collagen from skins of red tilapia was extracted by a series of washings with 0.1 M NaOH followed by enzyme-aided extraction for 24 hrs at 5° C. The colloidal suspension was salted out with NaCl and freeze-dried. Enzymes used were pepsin, trypsin and papain. Storage study of red tilapia skins was also carried out to determine the effects of frozen storage on collagen characteristics. Visually, all collagen samples were appeared to be similar and the differences could only be detected by chemical analyses such as protein content, amino acid composition, molecular weight profile and mineral content. The collagens from different enzymes extraction and storage period were snowy white and light-textured in appearance. The collagen yield was in the range 32.54% to 74.77% with pepsin digested collagen showing the highest yield. However, the protein content of pepsin digested collagens was much lower compared to trypsin and papain digested collagens. Protein content recorded was in the range 15% to 30%. Amino acid content of trypsin and papain digested collagen are higher than pepsin digested collagen. Apparent molecular weights of peptide detected were in the range 20,000 Da to 222,000 Da. In the mineral analysis, four elements were detected in all collagen samples namely carbon, oxygen, sodium and chlorine. SEM observations of all collagen samples show similar network structure. The collagen fibres are long cylindrical protein embedded in the protein matrix. Based on the results, trypsin digested collagen showed the best results in terms of protein content and amino acid profile but gave a low yield. Pepsin digested collagen on the other hand showed high yields but lower protein and amino acid content. Therefore, papain which showed reasonably high yield, protein and amino acid content will be chosen for the study of effects of enzyme on gelatin extraction and characteristics in the next chapter. Papain, being a plant based enzyme will also overcome the religious issues associated with certain communities such as Islam and Judaism. In the storage study, frozen storage of tilapia skins does not have significant effects on the collagen characteristics. Therefore, skins may be stored frozen for weeks without much affecting the characteristics of the gelatin extracted.

The invention claimed is:

1. A process of extracting collagen from skins of fish selected from the group consisting of *Lates calcarifer* (barramundi) and *Oreochromis nilotica* (red tilapia) using papain, comprising:
   a) homogenizing the fish skin with sodium hydroxide;
   b) obtaining a suspension from step (a);
   c) stirring the suspension for at least 24 hours;
   d) centrifuging the suspension from step (c) for at least 20 minutes;
   e) separating a precipitate from step (d);
   f) homogenizing the precipitate from step (e) with alkaline solution;
   g) stirring the precipitate from step (f) for at least 24 hours and for at least 3 repeats;
   h) washing the precipitate with water and acetic acid solution;
   i) stirring the precipitate from step (h) with papain at a working temperature of 5° C. for at least 24 hours;
   j) separating a papain-treated precipitate from step (i);
   k) centrifuging the papain-treated precipitate from step (j) for at least 20 minutes;
   l) separating collagen fibers from the centrifuged papain-treated precipitate of step (k);
   m) introducing the collagen fibers into a sodium chloride solution;
   n) collecting the collagen fibers from step (m) and centrifuging the collagen fibers for at least 20 minutes;
   o) separating the resulting collagen pellet;
   p) freeze-drying the collagen fibers from step o; wherein the collagen yield of said skins is between 14 and 40% by weight.

2. The process of claim 1, wherein said skin is obtained by cutting the skin from fresh or frozen fish.

* * * * *